United States Patent [19]

Kraig

[11] Patent Number: 4,700,709
[45] Date of Patent: Oct. 20, 1987

[54] APPARATUS AND METHOD FOR DETERMINING AMMONIUM ION CONCENTRATION AND TOTAL AMMONIA CONCENTRATION IN FLUIDS OR TISSUE

[75] Inventor: Richard P. Kraig, New York, N.Y.

[73] Assignee: Cornell Research Foundation, Inc., Ithaca, N.Y.

[21] Appl. No.: 824,349

[22] Filed: Jan. 30, 1986

[51] Int. Cl.[4] .................................................. A61B 5/00
[52] U.S. Cl. ..................................... 128/635; 204/403; 204/406; 204/408; 204/416; 204/431
[58] Field of Search ........ 128/635; 204/403, 406–408, 204/412, 415, 416, 431, 433

[56]  References Cited

U.S. PATENT DOCUMENTS

| | | | |
|---|---|---|---|
| 3,649,505 | 3/1972 | Strickler et al. | 204/415 |
| 3,763,422 | 10/1972 | MacPhee et al. | 324/438 |
| 3,830,716 | 8/1974 | Riseman et al. | 204/415 |
| 3,869,354 | 3/1975 | Montalvo | 204/1 T |
| 4,272,245 | 6/1981 | Diamond et al. | 436/68 |
| 4,338,174 | 7/1982 | Tamura | 128/635 X |
| 4,353,789 | 10/1982 | Kashkai | 204/409 |
| 4,440,620 | 4/1984 | Ono et al. | 204/403 |
| 4,452,682 | 6/1984 | Takata et al. | 204/403 |
| 4,486,290 | 12/1984 | Cohalan et al. | 128/635 X |

OTHER PUBLICATIONS

Nazar, B. L., et al., Analytical Biochemistry 95, 507–511 (1979).

Microelectrodes, Inc. Catalog titled "pH Oxygen Carbon Dioxide Ammonia Sodium Potassium" (undated).
Microelectrodes, Inc., Operating Instructions for MI-740 Micro Ammonia Electrode (undated).
Kraig, R. P., et al., Neuroscience Abstracts, vol. 11, p. 1301, "Interrelation of Bicarbonate & Ammonia Changes in Spreading Depression", Abstract 380.5, (10/85).

Primary Examiner—Lee S. Cohen

[57] ABSTRACT

Apparatus comprising an ammonia electrode, a pH electrode and a thermistor is utilized in determining ammonium in concentration and total ammonia concentration by simultaneously measuring to produce signals related to ammonia concentration, hydrogen ion concentration and temperature. Ammonium ion concentration and total ammonia concentration are calculated based on the equation $[NH_4^+]=[NH_3][H^+]/K$ where K is the equilibrium constant for the reaction $NH_3+H^+\rightleftharpoons NH_4^+$ at the temperature measured by the thermistor. In a preferred embodiment a microprocessor is included for the calculation of ammonium ion concentration and of total ammonia concentration. In one embodiment, the electrodes and thermistor are simultaneously applied to a body fluid or tissue of a living animal and continuous data on ammonium ion concentration and total ammonia is produced. Alternatively, fluid samples can be withdrawn from an animal or person for similar measurements in vitro.

18 Claims, 2 Drawing Figures

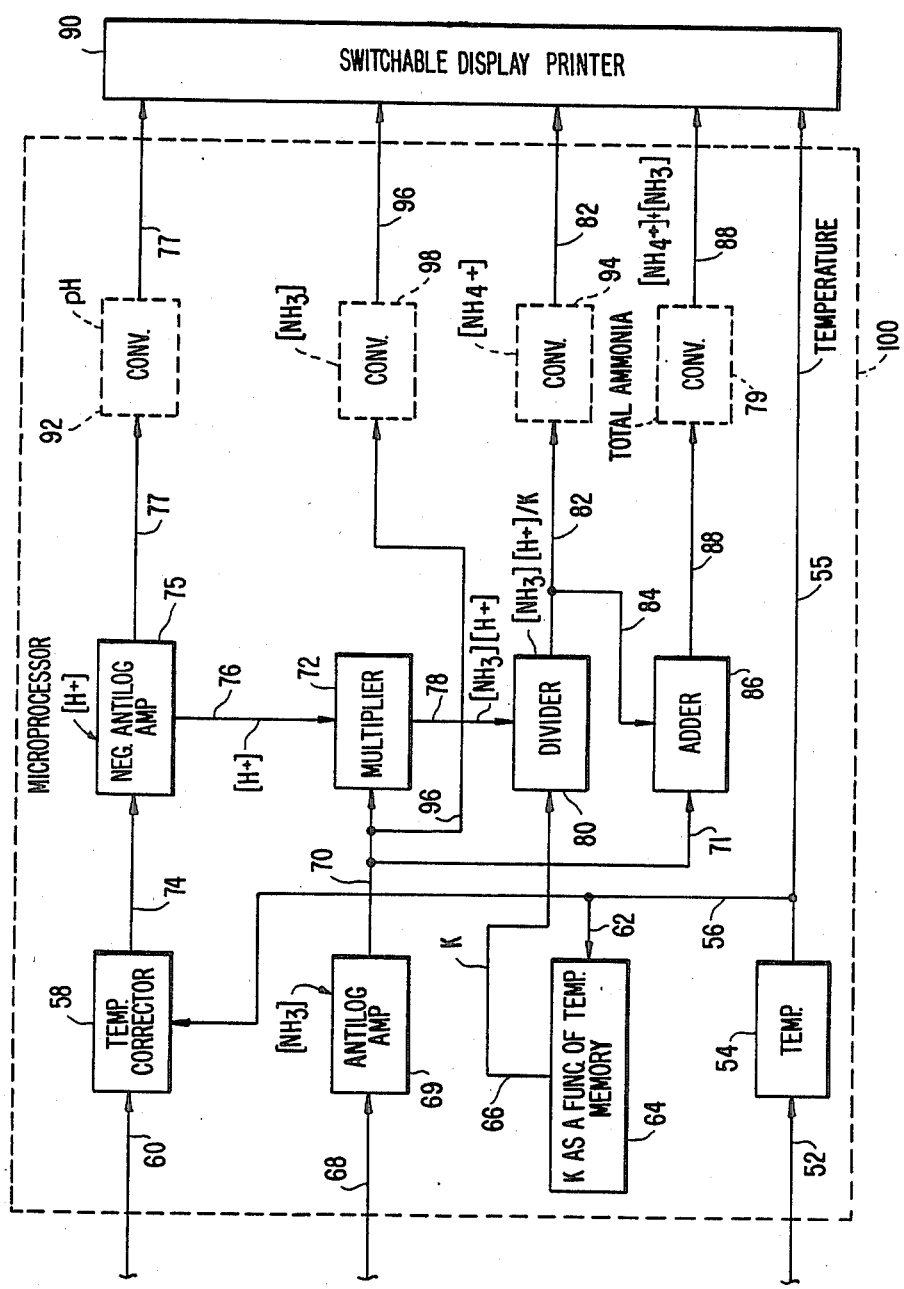

APPARATUS AND METHOD FOR DETERMINING AMMONIUM ION CONCENTRATION AND TOTAL AMMONIA CONCENTRATION IN FLUIDS OR TISSUE

This invention was made under and is subject to the terms and conditions of DHHS-NINCDS Grant No. 19108-03.

TECHNICAL FIELD

This invention is directed to apparatus and method for determining ammonium ion concentration and total ammonia concentration in fluids, e.g. body fluids such as human blood, or tissue.

BACKGROUND OF THE INVENTION

Measurements of concentrations of ammonia, ammonium ion and total ammonia (i.e. the total of the concentrations of ammonia and ammonium ion) are especially useful for the analysis of human blood samples for the diagnosis and treatment of certain metabolic encephalopathies (general deterioration of intellectual function) where blood levels of these become elevated.

For example, elevated blood levels of ammonia, ammonium ion and total ammonia are associated with liver failure from toxins (cirrhosis), infections (hepatitis, Reyes syndrome), hepatic tumors and cardiovascular system dysfunction (congestive heart failure or cor pulmonale). Furthermore, hyperammonia associated with intellectual deterioration can result in epileptics on treatment with valproic acid. Moreover, urinary bladder infections can produce metabolic encephalopathy due to excessive ammonia production by bacteria in the bladder. In the case of liver disease, treatment can involve nutritional treatment as well as administration of cathartics to eliminate ammonia producing bacteria from the bowel. In the valproic acid induced condition, the level of this drug is reduced or eliminated to ameliorate the condition. In the case of bladder infection, the infection is treated e.g. with antibiotics. In all these cases, the measurements as mentioned not only have a diagnostic function but also have a therapeutic function in that they allow determination of whether treatment is effective. Quick and accurate measurements are important because these conditions can lead to coma and death.

Furthermore, the aforementioned measurements can provide indirect but dynamic information about brain neutrotransmitter metabolism of glutamate and aspartate, for example, from direct brain measurements of ammonia/ammonium ion/total ammonia and pH changes.

At physiological pH levels most ammonia exists as ammonium ion ($>99\%$). Thus measurement of ammonium ion concentration is a good estimate of total ammonia content of blood, urine, brain, etc. The best measurement is the sum of ammonium ion concentration and ammonia concentration which is denoted total ammonia both herein and commonly.

Conventionally ammonium ion concentration is measured by an antibiotic based electrode. However, such electrodes do not discriminate between ammonium ion and other monovalent cations sufficiently to allow ammonium ion measurements in biological samples where such interfering ions are present in excess.

Montalvo U.S. Pat. No. 3,869,354 discloses measuring ammonium ion concentration by utilizing a monovalent cationic electrode surrounded with an ammonia permeable but otherwise cation impermeable membrane for selectivity and achieving sensitivity by placing the cation electrode assembly in the test solution and buffering the test solution to the same pH as that of the buffer electrolyte between the covering membrane and electrode.

Strickler et al. U.S. Pat. No. 3,649,505 discloses measuring total ammonia by measuring for ammonia after raising the pH to 11.5 or higher for samples of low total ammonia content.

The methods involving pH adjustment are inconvenient and require buffering or pH adjustment to levels which degrade biological tissues. Furthermore, pH adjustments are not possible when measurements are being made on tissue in vivo.

SUMMARY OF THE INVENTION

The present invention relies on an ammonia concentration measuring electrode, a hydrogen ion concentration measuring electrode and temperature measuring means to simultaneously measure ammonia concentration, hydrogen ion concentration and temperature in a fluid (e.g. a body fluid such as blood or urine) or in body tissue to provide data for calculating ammonium ion concentration and total ammonia concentration (ammonium ion concentration plus ammonia concentration) and preferably utilizes a microprocessor to effect the calculating. The apparatus and method herein do not have selectivity problems, are much more highly sensitive than conventional techniques and function without the need for pH adjustment regardless of the level of total ammonia present. Furthermore, the present invention can be used for continuous in vivo measurements in fluids and tissues or in vitro measurements on isolated fluids and tissues.

In particular the apparatus herein which is useful for measuring ammonia concentration, ammonium ion concentration and total ammonia concentration (ammonia concentration plus ammonium ion concentration) as well as hydrogen ion concentration in a fluid or body tissue comprises (a) a sensor comprising an ammonia concentration measuring electrode for contacting said fluid or tissue and producing an output signal related to ammonia concentration therein, (b) a sensor comprising a hydrogen ion concentration measuring electrode for contacting said fluid or tissue and producing an output signal related to hydrogen ion concentration therein, (c) temperature measuring means for contacting said fluid or tissue and producing an output signal related to temperature therein.

Preferably the element (a) comprises an ammonia electrode, the element (b) comprises a pH electrode, and the element (c) comprises a thermistor.

Preferably, the ammonia concentration measuring electrode produces an output signal proportional to the log of ammonia concentration in said fluid or tissue and the hydrogen ion measuring electrode comprises a glass pH electrode which produces an output signal which is proportional to the negative log of hydrogen ion concentration in said fluid or tissue.

Preferably, the apparatus herein also includes means for correcting the hydrogen ion concentration represented by the output signal of element (b) for the temperature of the sample and for producing an output signal representing temperature corrected hydrogen ion concentration.

Preferably in the apparatus herein the element (a) includes an ammonia permeable membrane made of, for example, polytetrafluoroethylene (e.g. Chemfluor lab tape by Chemplast, Inc.), polypropylene (e.g. from Microelectrodes, Inc.), collodion, 40% levane/60% methionine, silastic plastic (e.g. from Instrumentation Labs, Inc.), or silicone polycarbonate (e.g Type XD-7 powder from General Electric), and the apparatus includes means for passing a pulse of voltage into the fluid or tissue being analyzed whereby a deflection in the output signal from element (a) indicates said membrane has become impaired so that its pores permit passage of water and ions causing errors in the output signal from element (a) and should be changed.

The apparatus herein is used by simultaneously contacting the fluid or body tissue being analyzed with the ammonia concentration measuring electrode, the hydrogen ion concentration measuring electrode and the temperature measuring means and utilizing the output signals therefrom to calculate the ammonium ion concentration from the equation $[NH_4^+] = ([NH_3][H^+]/K)$ where $K$ is the equilibrium constant for the reaction $NH_3 + H^+ \rightleftharpoons NH_4^+$ at the temperature measured by the temperature measuring means. The concentration of total ammonia is calculated by adding the concentration of ammonium ion as calculated to the concentration of ammonia which is sensed. The apparatus can be utilized to continuously measure ammonia concentration, ammonium ion concentration, total ammonia concentration and pH in tissue or body fluid in a living animal (e.g. in mammals including humans) by continuously contacting the tissue or fluid with the elements (a), (b) and (c) and monitoring and/or recording the results. Isolated samples of fluid or tissue can also be similarly analyzed.

The apparatus herein preferably includes a microprocessor programmed to make the temperature correction in the sensed hydrogen ion concentration and to carry out the aforementioned calculations.

BRIEF DESCRIPTION OF THE DRAWING

FIGS. 1A and 1B of the drawing taken together are a schematic of preferred apparatus herein.

DETAILED DESCRIPTION

Figure 1A:
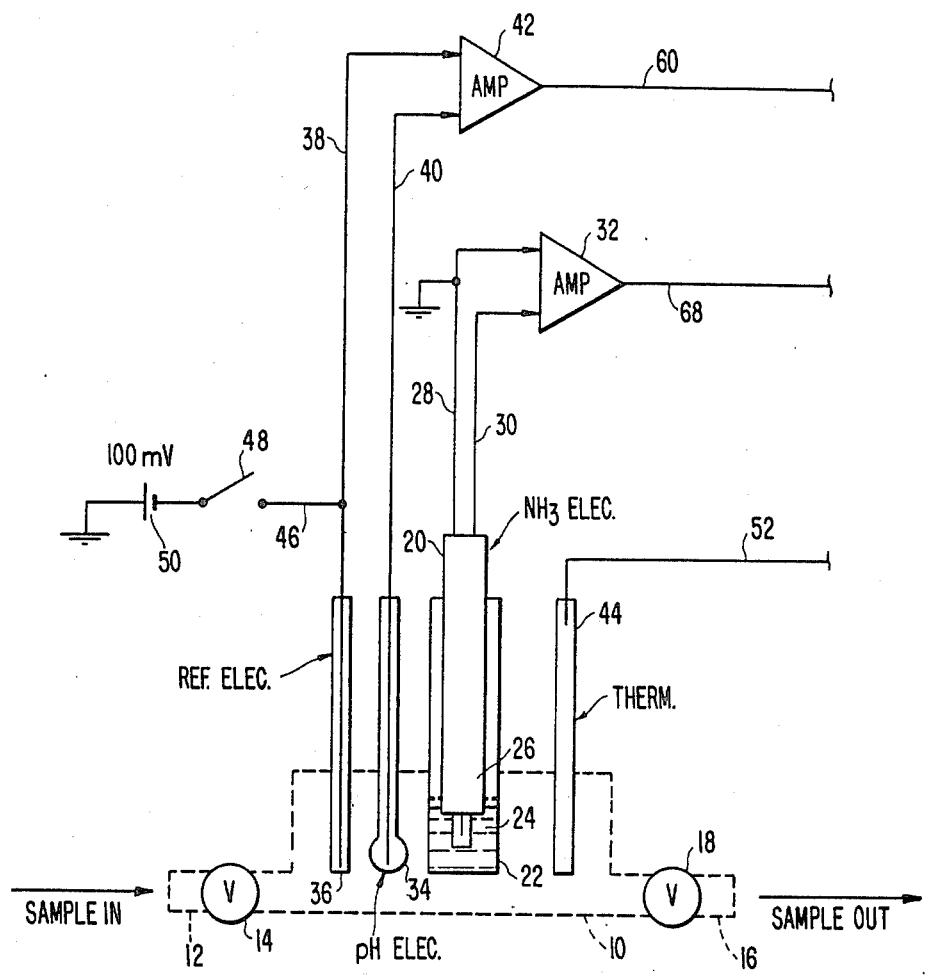

With continuing reference to the figures of the drawing, preferred apparatus herein includes a chamber 10 having an inlet 12 containing a valve 14 and an outlet 16 containing a valve 18.

Inserted into the chamber 10 is an ammonia concentration measuring electrode 20 (denoted "NH₃ ELEC."). This electrode 20 preferably is of a conventional design and has a membrane cover 22 which permits passage only of ammonia gas and contains a body 24 of internal electrolyte (usually ammonium chloride/sodium chloride solution) which changes pH in response to NH₃ admission through membrane cover 22. An internal combination pH electrode 26 (including a glass pH electrode and a reference electrode) is positioned in the body 24 of ammonium chloride/sodium chloride internal solution and produces an output signal in millivolts (mV) proportional to the pH of the internal electrolyte and also proportional to the log of ammonia concentration in the sample in accordance with the formula $mV = A \log [NH_3] + C$ where $A$ is the response of the pH electrode to a ten fold change in ammonia concentration and $C$ is an electrical constant of the system. A lead 28 from the reference electrode and a lead 30 from the glass pH electrode carry output signals from these to an instrumentation amplifier 32 (denoted "AMP.") which corrects for stray signals as determined by the reference electrode and produces the output signal of the combination electrode 26. Lead 28 also goes to ground.

A preferred electrode 20 is an MI-740 Micro Ammonia Electrode available from Microelectrodes, Inc. of Londonderry, N.H.; the polypropylene membrane which is typically used on the as purchased electrode can be replaced with a polytetrafluoroethylene (Teflon) membrane (e.g. of Chemfluor lab tape by Chemplast, Inc.). The membrane substitution changes the response time of the MI-740 electrode from 50 seconds to 10 seconds. However, other similar microporous membranes are useful and can be more advantageous in certain conditions as in measurements on blood samples.

Also inserted into the chamber 10 is a hydrogen ion measuring electrode comprising a conventional glass pH electrode 34 (denoted "pH ELEC.") and a reference electrode 36 (denoted "REF. ELEC."). A lead 38 from reference electrode 36 and a lead 40 from glass pH electrode 34 respectively carry signals from the electrodes to an instrumentation amplifier 42 (denoted "AMP.") which corrects for stray signals as determined by reference electrode 36 and produces an output signal in millivolts (mV) which is proportional to the negative log of hydrogen ion concentration in the sample. Preferably a combination electrode is used for the glass pH electrode and the reference electrode; a very suitable combination electrode is an MI-410 Micro-Combination pH Probe available from Microelectrodes, Inc. of Londonderry, N.H..

Also inserted into chamber 10 is a temperature measuring means in the form of a micro thermistor 44 (denoted "THERM.") which produces an output signal related to temperature of the sample.

A lead 46 junctions with lead 38 and includes a switch 48 and leads to a source of voltage 50, e.g. 100 mV. Closing and then opening of the switch 48 injects a pulse of voltage via reference electrode 36 into the sample being analyzed. Deflection in the output of amplifier 32 on closing of switch 48 indicates that the pores of membrane 22 have become enlarged (e.g. by hydration and or stretching) to the point where water and ions can pass therethrough resulting in inaccurate measurement and reveals that the membrane should be replaced with one that is not impaired.

The output signal from thermistor 44 is carried via a lead 52 to a converter 54 (denoted "TEMP.") which converts the output signal to the temperature represented by the signal. The output signal of converter 54 is carried by a lead 55 to a lead 56 and to a display/printer printer 90.

The lead 56 carries output signal of converter 54 to temperature corrector 58 (denoted "TEMP. CORRECTOR"), and a lead 60 carries the output of amplifier 42 to temperature corrector 58. The temperature corrector 58 corrects the hydrogen ion concentration as signaled by amplifier 42 for the temperature sensed by the thermistor 44 according to the Nicholsky equation.

A lead 62 junctions with lead 56 and carries the output signal from the converter 54 to a memory unit 64 (denoted "K AS A FUNC. OF TEMP. MEMORY") which stores data relating temperature and the ionization equilibrium constant, $K$, for the equation $[NH_4^+]=[NH_3][H^+]/K$ and in response to an input signal via lead 62 representing temperature sensed in the sample produces an output signal in a lead 66 representing the K value corrected for the temperature sensed. The K values stored in memory 64 are those corrected for temperature by a linear regression equation of the Arrhenius plot of K versus 1/T:

$$-\log K = \frac{2.7257 \cdot 10^3}{T} + 9.8270 \times 10^{-2}$$

where T is temperature in degrees Kelvin and are readily obtained from published tables and are stored in the memory associated with corresponding temperatures so that an input signal via lead 62 representing temperature sensed in the sample causes selection of temperature corrected K value and the production of an output signal in lead 66 representing temperature corrected K value.

A lead 68 carries the output signal of amplifier 32 (proportional to log ammonia concentration in the sample) to an antilog amplifier 69 (denoted "ANTILOG AMP") which converts the output signal of amplifier 32 to a signal proportional to ammonia concentration. The output signal of antilog amplifier 69 is carries via a lead 70 to a multiplier 72. A lead 74 carries the output signal of temperature corrector 58 (proportional to the negative log of hydrogen ion concentration in the sample) to a negative antilog amplifier 75 (denoted "NEG. ANTILOG AMP") which converts the output signal of temperature corrector 58 to a signal proportional to hydrogen ion concentration. A lead 76 carries the output signal of amplifier 75 to the multiplier 72. The multiplier 72 multiplies the output signals from amplifiers 69 and 75 to produce an output signal in a lead 78 proportional to the product of the signals, i.e. to $[NH_3][H^+]$.

The output signal of multiplier 72 (proportional to $[NH_3][H^+]$) is carried by lead 78 to a divider 80. The output signal of memory 64 (proportional to K corrected for the temperature sensed by thermistor 44) is carried by lead 66 to the divider 80. The divider 80 divides the signal received via 78 by the signal received via 66 to produce an output signal in lead 82 proportional to the quotient of the signals or to $[NH_3][H^+]/K$ or to $[NH_4^+]$, i.e. proportional to the ammonium ion concentration in the sample.

The output of divider 80 (proportional to $[NH_4^+]$) carried by lead 82 via junctioning lead 84 to an adder 86. The output of amplifier 69 (proportional to $[NH_3]$) is carried by lead 70 and 71 to adder 86. The adder 86 adds the signals to produce an output signal in a lead 88 related to $[NH_4^+]$ plus $[NH_3]$, i.e. total ammonia.

The output signal of negative antilog amplifier 75 (proportional to $[H^+]$ in the sample) is carried via lead 77 to switchable display/printer 90 which can display either the millivolts representing the signal or the output signal of amplifier 75 can optionally first be converted by a converter 92 (denoted "CONV.") to a signal representing pH in the sample so the unit 90 displays/prints pH.

The output signal of divider 80 (proportional to $[NH_4^+]$) is carried by lead 82 to display/printer 90 which can display the millivolts representing the signal or the output signal of divider 80 can optionally first be converted to a signal representing $[NH_4^+]$ by a converter 94 (denoted "CONV") so that the unit 90 displays/prints $[NH_4^+]$.

The output signal of amplifier 69 (proportional to $[NH_3]$) is carried via lead 70 and junctioning lead 96 to display/printer 90 which can display millivolts representing the signal or said output signal can optionally first be converted by a converter 98 (denoted "CONV.") to a signal representing $[NH_3]$ so the unit 90 displays/prints $[NH_3]$.

The output signal of adder 86 (representing total ammonia concentration in the sample) is carried by lead 88 to display/printer 90 which can display/print either millivolts or can optionally first be converted by a converter 79 (denoted "CONV.") to a signal representing total ammonia concentration in the sample so the unit 90 displays/prints total ammonia.

The output signal of converter 54 is carried by lead 55 to display/printer 90 which can display/print the temperature in the sample as represented by the signal.

The converters 92, 94, 98, and 79 are depicted in dashed lines because they are only necessary if it is desired to display/print pH and concentrations rather than millivolts representing these.

The elements within the dashed line box 100 can be components of a conventional microprocessor programmed to perform the indicated functions.

The display/printer 90 is switchable to display and/or print data on any or all of total ammonia concentration, $[NH_4^+]$, $[NH_3]$, pH, and temperature.

As used herein $[NH_4^+]$ means ammonium ion concentration in the sample, $[NH_3]$ means ammonia concentration in the sample, $[H^+]$ means hydrogen ion concentration in the sample, pH means pH of the sample, temperature means temperature of the sample and total ammonia means the total of $[NH_3]$ and $[NH_4^+]$ in the sample.

In use on fluid samples, a sample is introduced via inlet 12 to fill chamber 10 and valve 18 is used to provide sufficient back pressure to provide the response time for the functioning of electrode 20. If desired, the sample can be fed continuously through the chamber 10 to provide continuous data for display/printer 90. The electrodes 34, 36 together with amplifier 42 provide an output signal proportional to the negative log of hydrogen ion concentration in the sample. The electrode 20 together with amplifier 32 provides an output signal proportional to log ammonia concentration in the sample. The thermistor 44 provides an output signal related to temperature in the sample. The microprocessor 100 corrects the hydrogen ion concentration sensed for the temperature sensed according to the method hereinbefore described and calculates the ammonium ion concentration in the sample and the total ammonia concentration in the sample according to equations hereinbefore described and feeds this and other information to the display/printer for display/printing of data on at least total ammonia concentration in the sample and if desired the concentrations of ammonium ion and ammonia and the pH and temperature in the sample.

The chamber 10 is depicted in dashed lines to indicate that it can be deleted for use of the apparatus herein where a fluid sample is in a different container or where analysis is carried out on body tissue. For measurements on tissue the electrodes 34 and 36 and electrode 20 and thermistor 44 are simultaneously applied to contact a tissue sample or tissue in a living animal (e.g. mammals including humans) and concentrations can be measured and monitored continuously.

If the chamber 10 is used, it preferably has a volume, e.g. of 100 μl, which is sufficient to provide contact space for the preferred electrodes herein. Alternatively the chamber can be larger if needed.

As indicated above the apparatus herein functions to provide analysis of total ammonia and ammonium ion in samples without the need to adjust pH thereof.

The apparatus herein can provide greater sensitivity than has heretofore been reported for ammonium ion concentration measurement. The apparatus herein with the preferred electrodes as described has a theoretical sensitivity to ammonium ion and total ammonia greater than 0.1 nmoles. This is based on the fact that the sensitivity of the ammonia electrode has been measured to be $0.3 \times 10^{-6}$ M/l and the sample volume for pH measurement is preferably at least 100 $\mu$l. While under biological conditions, i.e. concentrations normally seen in blood, urine or brain tissue, such high sensitivity is not needed, the high sensitivity herein can be uniquely useful to obtain measurements on very small samples. To obtain high sensitivities, the samples should be analyzed in a closed container to prevent egress of ammonia.

As indicated above, the apparatus and method of the invention in a preferred embodiment have a safeguard against inaccuracies due to ion interference since the membrane can be checked utilizing pulsed voltage by closing switch 48. While a voltage of 100 mV has been mentioned for this test, as a more than adequate level of stimulation, voltages ranging for example, from 10 to 250 mV are readily used.

Reproducibility is as high as sensitivity.

The following Example is illustrative of the invention herein. In the Example, [H+] is hydrogen ion concentration, $PCO_2$ is the arterial partial pressure of carbon dioxide, $PO_2$ is the arterial partial pressure of oxygen, and $PtCO_2$ is the brain tissue partial pressure of carbon dioxide.

EXAMPLE

Rats were anesthetized with halothane and spontaneously ventilated; warmed to 37° C.; and an artery cannulated. Parietal cortex was exposed and superfused with Ringer. Arterial pressure, pH, $PCO_2$, $PO_2$, and glucose were stabilized. Spreading depression was elicited by a 1-3 sec, 100 Hz stimulus to nearby cortex. [H+] and $PtCO_2$ and [H +] and [$NH_3$] were monitored in pairs. [H+] measuring microelectrodes (tridodecylamine) were placed 300 $\mu$m below and $PtCO_2$ or [$NH_3$] measuring electrodes at the pial surface.

Temporal changes were compared to the negative dc shift of spreading depression (indicating brain silence). [H+] changes began simultaneously with the dc shift and consisted of a brief alkaline, then acid shift. [H+] was 7.30±0.01 pH (based on averaging 33 measurements) before spreading depression initiation and became more acid in 9±1 seconds to reach a peak of 6.93±0.02 pH (36±1 seconds) before returning to baseline 11.9±0.8 minutes later. $PtCO_2$ changes began 11±2 seconds (based on averaging 12 measurements) after the dc shift started; reached a peak in 37±2 seconds; and returned to baseline in 6.6±1.3 minutes. [$HCO_3^-$] changes were calculated from these measured variables and showed that [$HCO_3^-$] first rose with the alkaline spike and then reached a low of 13.6±0.6 mM (between 9-37 seconds after the dc shift) and returned to baseline in 11.9±0.8 minute. [$NH_3$] changes were more delayed and prolonged. Spreading depression initiation produced a small rise in [$NH_3$] from 2.3±0.1 $\mu$M (based on averaging 20 measurements), but with the achieving of the condition, [$NH_3$] rose rapidly to reach a peak of 4.4±0.3 $\mu$M 1.8±0.1 minute after the dc shift began. Furthermore, 20.8±2.1 minutes elapsed before [$NH_3$] returned to baseline.

Temperature is monitored simultaneously with the monitoring of [H+] and [$NH_3$] and remains constant at 37±0.5° C.

Based on the above, [$NH_4^+$] is calculated utilizing the equation [$NH_4^+$]=[$NH_3$][H+]/K with K at 37° C. being $1.2859 \times 10^{-9}$. Based on these calculations the following is found: After initiation of spreading depression, there is a rise in [$NH_4^+$] from a concentration of 116 $\mu$M to 382 $\mu$M about 28 seconds after the dc shift and 12.5 minutes elapsed before returning to baseline. After initiation of spreading depression, there is a rise in total ammonia concentration from 118 $\mu$M to 386 $\mu$M about 1.8 minutes after the dc shift and about 20.8 minutes elapsed before returning to baseline.

These results show for the first time that during spreading depression rapid and focal changes in [$HCO_3^-$] and [$NH_3$], [$NH_4^+$] and total ammonia concentration can occur in brain. The delayed changes in [$NH_3$], [$NH_4^+$] and total ammonia concentration imply that they are a response to the rise in [H+] and $PtCO_2$. Furthermore, these results are the first report of direct and continuous measurements of [$NH_3$] [$NH_4^+$], and total ammonia in living tissue. These results document the unique utility of this invention. The conventional technique for carrying out testing in spreading depression would have involved periodic biopsies, freezing these and measuring at a later time, a much more complicated and less accurate procedure.

As used herein, the term "animal" includes "mammals" which includes "humans".

Other variations will be evident to those skilled in the art. For example, while the preferred temperature measuring means is a thermistor which is small and very sensitive, other temperature measuring means, e.g. a thermocouple, are also useful. Therefore, the scope of the invention is intended to be defined by the claims.

What is claimed is:

1. Apparatus for determining the concentration of ammonium ion in fluid or tissue without adjusting the pH thereof, said apparatus comprising
   (a) an ammonia concentration measuring electrode for contacting said fluid or tissue and producing a first output signal related to ammonia concentration therein,
   (b) a hydrogen ion concentration measuring electrode for contacting said fluid or tissue and producing a second output signal related to hydrogen ion concentration therein,
   (c) temperature measuring means for contacting said fluid or tissue and producing a third output signal related to temperature therein,
   (d) means for calculating ammonium ion concentration based upon said first, second and third output signals utilizing the equation $$[NH_4^+] = \frac{[NH_3][H^+]}{K}$$

where K is the equilibrium constant for the reaction $NH_3 + H^+ \rightleftharpoons NH_4^+$ at the temperature measured by element (c).

2. Apparatus as recited in claim 1 which also is for determining total ammonia concentration in said fluid or tissue which further includes means (e) for calculating total ammonia concentration by adding the ammonia concentration as measured by element (a) to the ammonium ion concentration as calculated by means (d).

3. Apparatus as recited in claim 2 wherein the means (d) and the means (e) constitute microprocessor means.

4. Apparatus as recited in claim 3 wherein said microprocessor means provides output signals related to ammonia concentration, pH, ammonium ion concentration, total ammonia concentration and temperature in said fluid or tissue.

5. Apparatus as recited in claim 4 which includes display means, printer means or combination display/printer means for displaying and recording at least one of ammonium ion concentration and total ammonia concentration in said fluid or tissue.

6. Apparatus as recited in claim 2 wherein the ammonia concentration measuring electrode produces an output signal proportional to the log of ammonia concentration in said fluid or tissue and wherein the hydrogen ion measuring electrode comprises a glass pH electrode which produces an output signal which is proportional to the negative log of hydrogen ion concentration in said fluid or tissue and wherein the means (d) and the means (e) constitute microprocessor means which receives said signals and the signal representing ammonium ion concentration and total ammonia concentration utilizing the equation $$[NH_4^+] = \frac{[NH_3][H^+]}{K}$$

where K is the equilibrium constant for the reaction $NH_3 + H^+ \rightleftharpoons NH_4^+$ at the temperature measured by element (c).

7. Apparatus as recited in claim 6 wherein said microprocessor means comprises means for correcting the hydrogen ion concentration represented by the output signal of element (b) for the temperature of the sample and producing an output signal representing temperature corrected hydrogen ion concentration.

8. Apparatus as recited in claim 7 wherein said microprocessor means also comprises negative antilog amplifier means for receiving the output of the means for correcting the hydrogen ion concentration and producing an output signal proportional to temperature corrected hydrogen ion concentration, antilog amplifier means for receiving the output signal of element (a) and producing an output signal proportional to ammonia concentration, multiplier means for receiving output signals of said negative antilog amplifier means and said antilog amplifier means and producing an output signal proportional to $[NH_3][H^+]$, memory means for storing the K values associated with corresponding temperatures and for receiving an input signal related to the temperature in the fluid or tissue and producing an output signal proportional to the K value corresponding to the temperature of the fluid or tissue, and divider means for receiving the output signals of the multiplier means and the memory means and producing an output signal which is the quotient of these and is proportional to ammonium ion concentration in the fluid or tissue.

9. Apparatus as recited in claim 8 wherein said microprocessor means also comprises adder means for receiving output signals from said antilog amplifier means and from said divider means and for adding these and producing an output signal proportional to total ammonia concentration in the fluid or tissue.

10. Apparatus as recited in claim 9 wherein element (a) includes an ammonia permeable membrane and wherein element (b) comprises a combination electrode including a reference electrode and a lead therefrom and additionally comprising means to pass a pulse of voltage into said lead and through said reference electrode into said fluid or tissue whereby a deflection in the output signal from element (a) on said passage of voltage into said fluid or tissue indicates said membrane has become impaired so that its pores permit passage of water and ions causing errors in the output signal from element (a) and should be changed.

11. A method for determining the concentration of ammonium ion in fluid or tissue without adjusting the pH thereof, said method comprising the steps of
 (a) measuring the ammonia concentration in said fluid or tissue comprising contacting said fluid or tissue with a sensor producing an output signal related to ammonia concentration therein,
 (b) simultaneously measuring the hydrogen ion concentration in said fluid or tissue comprising contacting said fluid or tissue with a sensor producing an output signal related to hydrogen ion concentration therein,
 (c) simultaneously measuring the temperature of said fluid or tissue
 (d) calculating ammonium concentration utilizing the equation $$[NH_4^+] = \frac{[NH_3][H^+]}{K}$$

where K is the equilibrium constant for the reaction $NH_3 + H^+ \rightleftharpoons NH_4^+$ at the temperature measured in step (c).

12. Method as recited in claim 11 wherein the output signal of step (a) is proportional to the log of ammonia concentration and wherein the output signal of step (b) is proportional to the negative log of hydrogen ion concentration.

13. Method as recited in claim 11 wherein the output signal of step (b) is corrected based on the temperature measured in step (c).

14. Method as recited in claim 13 wherein said measurements are carried out continuously on a living animal.

15. A method for determining the concentration of total ammonia in fluid or tissue without adjusting the pH thereof, said method comprising the steps of
 (a) measuring the ammonia concentration in said fluid or tissue comprising contacting said fluid or tissue with a sensor producing an output signal related to ammonia concentration therein,
 (b) simultaneously measuring the hydrogen ion concentration in said fluid or tissue comprising contacting said fluid or tissue with a sensor producing an output signal related to hydrogen ion concentration therein,
 (c) simultaneously measuring the temperature of said fluid or tissue,
 (d) calculating the ammonium ion concentration utilizing the equation $$[NH_4^+] = \frac{[NH_3][H^+]}{K}$$

where K is the equilibrium constant for the reaction $NH_3 + H^+ \rightleftharpoons NH_4^+$ at the temperature measured in step (c).

(e) calculating total ammonia concentration by adding the ammonia concentration defined by the output signal of step (a) to the ammonium ion concentration calculated in step (d).

16. Method as recited in claim 15 wherein the output signal of step (a) is proportional to the log of ammonia concentration and wherein the output signal of step (b) is proportional to the negative log of hydrogen ion concentration.

17. Method as recited in claim 16 wherein the output signal of step (b) is corrected based on the temperature measured in step (c).

18. Method as recited in claim 17 wherein said measurements are carried out continuously on a living mammal.

* * * * *

UNITED STATES PATENT AND TRADEMARK OFFICE
CERTIFICATE OF CORRECTION

PATENT NO. : 4,700,709
DATED : 20 October 1987
INVENTOR(S) : RICHARD P. KRAIG

It is certified that error appears in the above-identified patent and that said Letters Patent is hereby corrected as shown below:

In the Abstract, at line 3, "ammonium in concentration" should be --ammonium ion concentration--

Claim 6 (column 9, line 26), after "the signal" insert --related to temperature and converts these signals into signals--

Claim 13 (column 10, line 46), change "claim 11" to --claim 12--

Signed and Sealed this

Fifth Day of April, 1988

Attest:

DONALD J. QUIGG

*Attesting Officer*  *Commissioner of Patents and Trademarks*